(12) United States Patent
Yabe et al.

(10) Patent No.: US 7,350,406 B2
(45) Date of Patent: Apr. 1, 2008

(54) SENSOR CHIP BREAKING STRENGTH INSPECTION APPARATUS AND SENSOR CHIP BREAKING STRENGTH INSPECTION METHOD

(75) Inventors: Hideki Yabe, Tokyo (JP); Yuichi Sakai, Tokyo (JP); Yoshitatsu Kawama, Tokyo (JP); Munehito Kumagai, Tokyo (JP); Yasuyuki Nakaoka, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/279,606

(22) Filed: Apr. 13, 2006

(65) Prior Publication Data
US 2007/0137310 A1 Jun. 21, 2007

(30) Foreign Application Priority Data
Dec. 8, 2005 (JP) .............................. 2005-354520

(51) Int. Cl.
*G01M 19/00* (2006.01)
(52) U.S. Cl. .................. 73/119 R; 73/12.07; 73/12.08
(58) Field of Classification Search .................. 73/116, 73/117.2, 117.3, 118.1, 118.2, 119 R, 12.01, 73/12.04, 12.05, 12.07, 12.08, 12.09
See application file for complete search history.

(56) References Cited

U.S. PATENT DOCUMENTS

| 4,848,198 A | * | 7/1989 | Royal et al. ................ 82/1.11 |
| 5,341,685 A | | 8/1994 | Malone |
| 6,230,569 B1 | | 5/2001 | Ball |

FOREIGN PATENT DOCUMENTS

| DE | 195 23 171 A1 | 4/1996 |
| JP | 09-033567 | * 7/1997 |
| JP | 2000-146734 A | 5/2000 |
| WO | 02-101348 A1 | 12/2002 |

* cited by examiner

*Primary Examiner*—Eric S. McCall
(74) *Attorney, Agent, or Firm*—Sughrue Mion, PLLC

(57) ABSTRACT

A sensor chip breaking strength inspection apparatus that performs sensor chip breaking strength inspection on a semiconductor wafer on which a plurality of sensor chips having a diaphragm portion are disposed includes: a stage on which the semiconductor wafer is mounted; and a nozzle that emits a medium onto the sensor chips at a pressure equivalent to a standard breaking strength of the sensor chips.

14 Claims, 11 Drawing Sheets

GAS (OR WATER) PRESSURE DISTRIBUTION

GAS (OR WATER)
PRESSURE DISTRIBUTION

REDUCED PRESSRE

REDUCED PRESSRE

SENSOR CHIP BREAKING STRENGTH INSPECTION APPARATUS AND SENSOR CHIP BREAKING STRENGTH INSPECTION METHOD

BACKGROUND OF THE INVENTION

1. Field of the Invention

The present invention relates to a sensor chip breaking strength inspection apparatus and sensor chip breaking strength inspection method for flow sensors, pressure sensors, and acceleration sensors that are used in automobiles, for example.

2. Description of the Related Art

Known examples of conventional sensor chip inspection apparatuses for semiconductor wafers in which sensor chips having diaphragm portions are lined up vertically and horizontally include those in which characteristics inspections of the sensor chips are performed by imparting a predetermined deforming force to the diaphragm portions by applying gas pressure to the diaphragm portions from a rear surface side of the sensor chips (see Patent Literature 1, for example).

Patent Literature 1

Japanese Patent Laid-Open No. HEI 9-33567 (Gazette)

However, although deformation in the diaphragm portions can be found by such a sensor chip inspection apparatus, one problem has been that it is difficult to find sensor chip breaking strength.

Specifically, considerable pressure must generally be applied to a sensor chip in order to find the sensor chip breaking strength, but the above sensor chip inspection apparatus has a construction in which gas pressure is imparted to an entire surface of the semiconductor wafer and if an attempt is made to apply a force equivalent to standard breaking strength to individual sensor chips, the force acting on the entire surface of the semiconductor wafer becomes large. Because of this, stresses are concentrated locally at portions where the semiconductor wafer is held mechanically, and one problem has been that individual sensor chip breaking strength cannot be inspected since the semiconductor wafer cannot withstand such forces and breaks.

Another problem has been that inspection apparatuses in which a force is applied to the semiconductor wafer by evacuating the inside of a chamber are unsuitable for sensor chip breaking strength inspection because pressure can only be applied to the semiconductor wafer up to atmospheric pressure.

Pressure greater than atmospheric pressure can be applied if the semiconductor wafer is placed inside a pressure chamber and then the semiconductor wafer is vacuumed, but one problem has been that a large-scale pressure chamber must be made for that purpose, increasing costs, and time spent on inspection is also increased:

SUMMARY OF THE INVENTION

The present invention aims to solve the above problems and an object of the present invention is to provide a sensor chip breaking strength inspection apparatus that can determine whether individual sensor chips are okay (OK) or no good (NG) by a simple construction.

Another object of the present invention is to provide a sensor chip breaking strength inspection method that enables sensor chip breaking strength inspection to be performed in a sensor chip cleaning process without requiring a sensor chip breaking strength inspecting process to be set up separately.

In order to achieve the above object, according to one aspect of the present invention, there is provided a sensor chip breaking strength inspection apparatus that includes: a stage on which a semiconductor wafer is mounted; and a nozzle that emits a medium onto sensor chips at a pressure equivalent to a standard breaking strength of the sensor chips.

According to another aspect of the present invention, there is provided a sensor chip breaking strength inspection method in which a medium is emitted at sensor chips at a pressure equivalent to a standard breaking strength of the sensor chips while cleaning during or after dicing of a semiconductor wafer on which the sensor chips are lined up vertically and horizontally.

Using a sensor chip breaking strength inspection apparatus according to the present invention, sensor chip breaking strength inspection can be performed using a simple construction.

Using a sensor chip breaking strength inspection method according to the present invention, sensor chip breaking strength inspection can be performed in a sensor chip cleaning process without requiring a sensor chip breaking strength inspecting process to be set up separately.

DETAILED DESCRIPTION OF THE PREFERRED EMBODIMENTS

Figure 1:
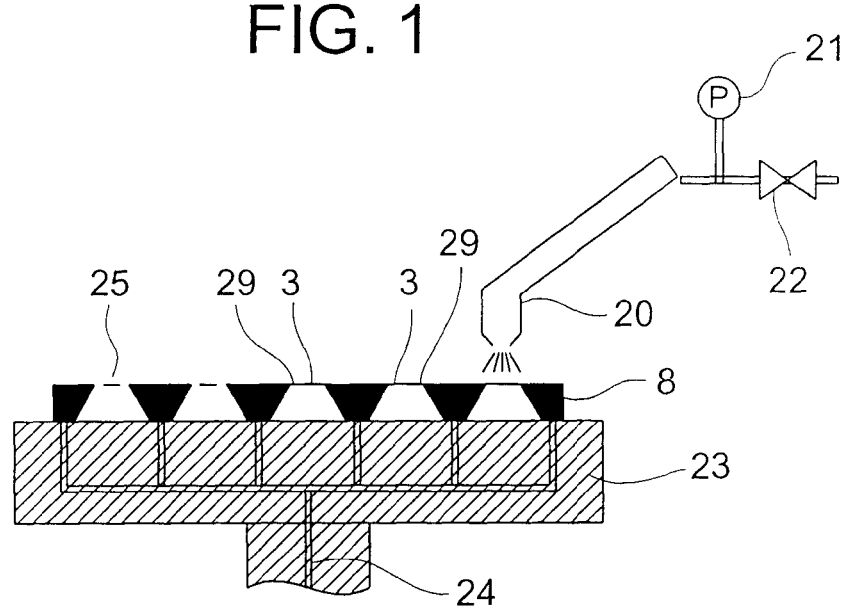
FIG. 1 is a schematic diagram showing a cross section of a sensor chip breaking strength inspection apparatus according to Embodiment 1 of the present invention.

Preferred embodiments of the present invention will now be explained based on drawings, and identical or corresponding members and portions in the drawings will be given identical numbering.

Embodiment 1

Figure 2:
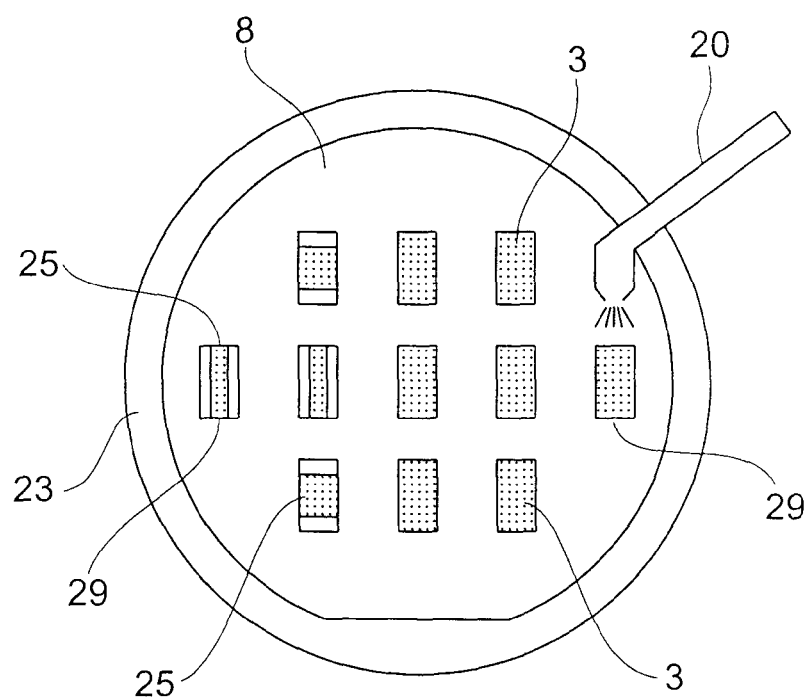
FIG. 2 is a plan showing the sensor chip breaking strength inspection apparatus from FIG. 1 when viewed from directly above.

FIG. 1 is a schematic diagram showing a cross section of a sensor chip breaking strength inspection apparatus according to the present invention, and FIG. 2 is a plan showing the sensor chip breaking strength inspection apparatus from FIG. 1 when viewed from directly above.

This sensor chip breaking strength inspection apparatus includes: a stage 23 on which a semiconductor wafer 8 is mounted; a nozzle 20 that has a tip directed at the semiconductor wafer 8 and emits a gas that constitutes a medium; a pressure gauge 21 that monitors pressure of the gas that is emitted from the nozzle 20; a pressure regulator 22 that adjusts the pressure of the gas that is emitted from the nozzle 20; and a vacuum line 24 that is disposed on the stage 23 and sucks the semiconductor wafer 8 on by vacuum.

Sensor chips 29 having diaphragm portions 3 that are made thinner centrally so as to deform easily are arranged vertically and horizontally on the semiconductor wafer 8. Patterned circuits for strain detection, for example, are formed on front surfaces of the sensor chips 29. This semiconductor wafer 8 is separated into individual sensor chips 29 by dicing after the patterned circuits are formed.

Moreover, bridge-shaped diaphragm portions 25 of a type in which vertical apertures pass through a portion of the diaphragm portion 3 are also included in this semiconductor wafer 8.

In this sensor chip breaking strength inspection apparatus, gas is emitted from the nozzle 20 over the entire semiconductor wafer 8 such that a gas pressure greater than or equal to atmospheric pressure that is equivalent to standard breaking strength for the sensor chips 29 is applied to the individual sensor chips 29. By applying this pressure having a value equivalent to the standard breaking strength to the diaphragm portions 3 and 25, sensor chips 29 that do not break can be used without modification, but because sensor chips 29 that cannot withstand this force and break do not satisfy standards, such sensor chips 29 are of course no good (NG).

Now, in the present invention, the pressure equivalent to the standard breaking strength is applied to the diaphragm portions 3 and 25 of all of the sensor chips 29, but one matter of concern in that case is whether sensor chips 29 to which pressure has been applied once have strength to withstand equal pressure when applied a second time.

In other words, by performing breaking strength inspection on all of the sensor chips 29, there is a risk that the strength of all of the sensor chips 29 may degrade, and even if standard breaking strength is satisfied at first, damage due to inspection may remain and the final products may not satisfy the standard breaking strength.

For this reason, inspections that subject all of the sensor chips 29 to pressure equivalent to the standard breaking strength have not been performed until now.

In regard to this, the present inventors found by experiment that strength degradation is not observed in the sensor chips 29 under repeated pressurization in the order of ten or more times.

Figure 3:
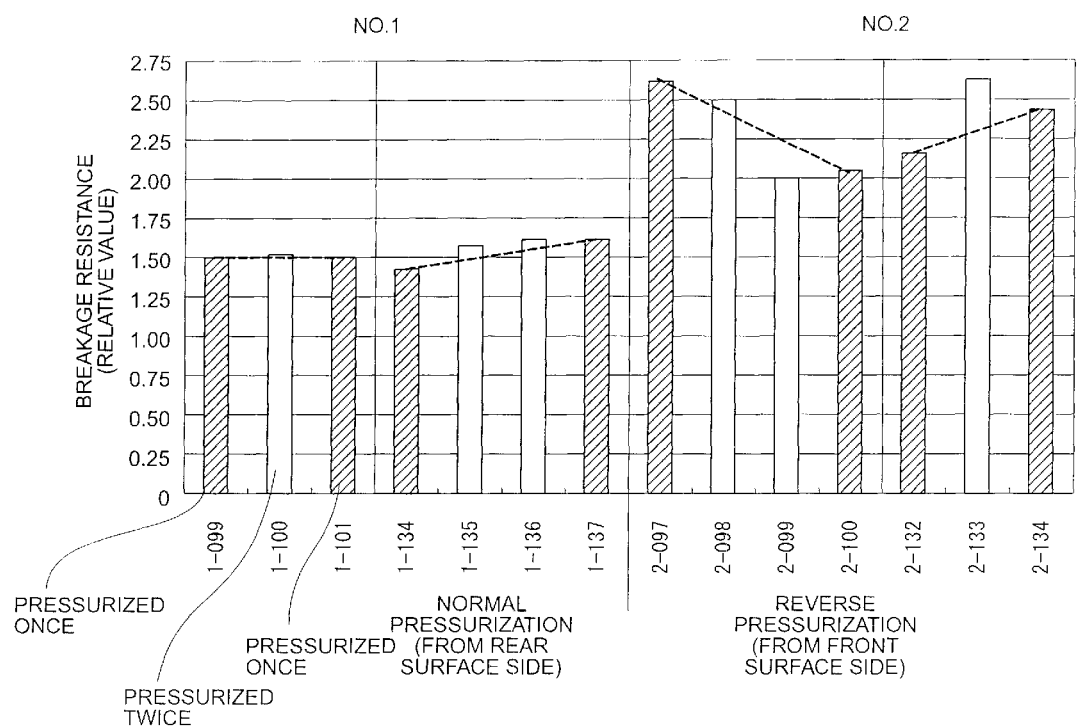
FIG. 3 is a graph showing experimental results of sensor chip breaking strength.

FIG. 3 is a graph showing results of that experiment.

In this experiment, a breaking strength experiment was performed on sensor chips 29 using a silicon target, mixing nitrogen gas into argon to approximately 30 percent, and using an Si—N film that was formed at a pressure of approximately 1.0 Pa at a sputtering power density of 5 W/cm$^2$.

Semiconductor Wafer No. 1 is an example in which pressure was applied to a semiconductor wafer from a rear surface, and Semiconductor Wafer No. 2 is an example in which pressure was applied to a semiconductor wafer from a front surface.

Moreover, values of breakage resistance between Semiconductor Wafer No. 1 and Semiconductor Wafer No. 2 differ, but this is because the original breakage resistance differed due to differences in lot and film thickness, etc., in the two semiconductor wafers, and not because breakage resistance from the rear of the sensor chips differs from breakage resistance from the front.

In FIG. 3, numerical values shown in the horizontal axis represent address numbers of the sensor chips on the semiconductor wafers, and for example, 1-099 represents Address No. 099 of the sensor chips 29 on Semiconductor Wafer No. 1, and 1-100 represents a sensor chip 29 adjacent to 1-099.

Numerical values shown in the vertical axis are relative values of strength values at which the sensor chips actually broke compared with the standard breaking strength.

Hatched bars in the graph represent maximum pressure withstood as relative values when a normal pressurization was performed once and the pressure was sequentially increased until the sensor chip broke. They indicate that when the force that was applied to a sensor chip from the rear surface of Semiconductor Wafer No. 1 was incremented by a relative value of 0.1, as in 0 to 1.0 to 1.1 to 1.2 to 1.3, etc., the sensor chip broke when the relative value was 1.5, for example.

In contrast, the white bars in the graph are results when pressurization was performed a plurality of times. They indicate that when pressures of equal value were applied to a sensor chip twice each while the force that was applied to the sensor chip from the rear surface of Semiconductor Wafer No. 1 was incremented by a relative value of 0.1, as in (0 to 1.5) to (0 to 1.5) to (0 to 1.6) to (0 to 1.6) to (0 to 1.7), etc., the sensor chips broke when the relative value was 1.5, for example.

Sensor chips that were adjacent to each other were used for the experiments, and the sensor chip breaking strength that is expressed by the white bars between the hatched bars can be considered to be close to the interpolated strength of the hatched bars (values along broken lines).

As can also be seen from the graph, sensor chip breaking strength changes very little even if pressurization is performed twice.

Moreover, the present inventors have also found by experiment that sensor chip breaking strength changes very little even if pressurization is repeated ten or more times.

In other words, it can be said that if pressure having a standard breaking strength value is applied to all of the sensor chips, sensor chips that do not satisfy the standard will break, but sensor chips that satisfy the standard breaking strength will maintain their original breaking strength values without the breaking strength value degrading.

Consequently, using a sensor chip breaking strength inspection apparatus according to Embodiment 1, sensor chips 29 that are selected as OK during the breaking strength inspection can be provided as products without modification without the breaking strength of the sensor chips 29 degrading after inspection even if the breaking strength inspection is performed on all of the sensor chips 29.

Moreover, in this embodiment, gas has been used for the medium, but water may also be used. Ultrasonic waves may also be used in combination with either the gas or the water. If ultrasonic waves are used in combination, it is sufficient for the pressure of the gas or water itself to be less than or equal to the standard because the breaking strength of the sensor chips 29 may change depending on the frequency and strength of the ultrasonic waves. If ultrasonic waves are used in combination, it is necessary to perform calibration for standard values separately.

Figure 4:
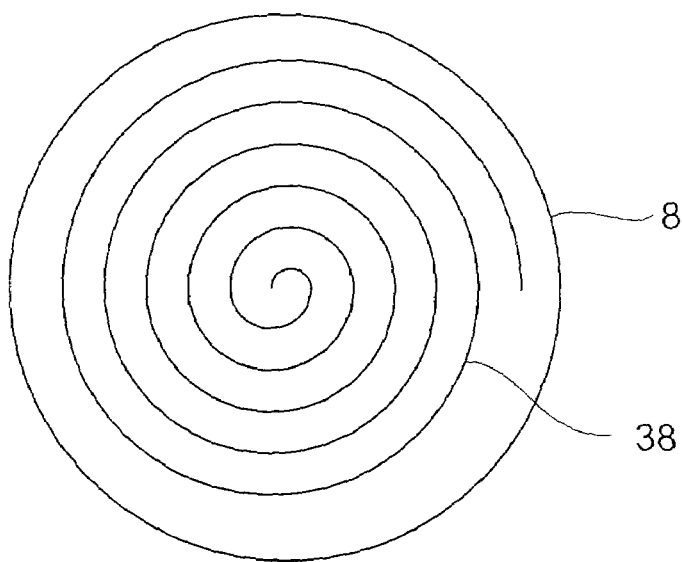
FIG. 4 is a schematic diagram in which an example of a path of a nozzle relative to a semiconductor wafer is shown.

FIG. 4 is a path 38 of the nozzle 20 that is drawn on the semiconductor wafer 8 if the nozzle 20 is moved transversely while rotating the semiconductor wafer 8. Here, the path 38 of the nozzle 20 exhibits a spiral path like a groove of a phonograph record, and enables the breaking strength of all of the sensor chips 29 disposed vertically and horizontally over the entire surface of the semiconductor wafer 8 to be inspected.

Figure 5:
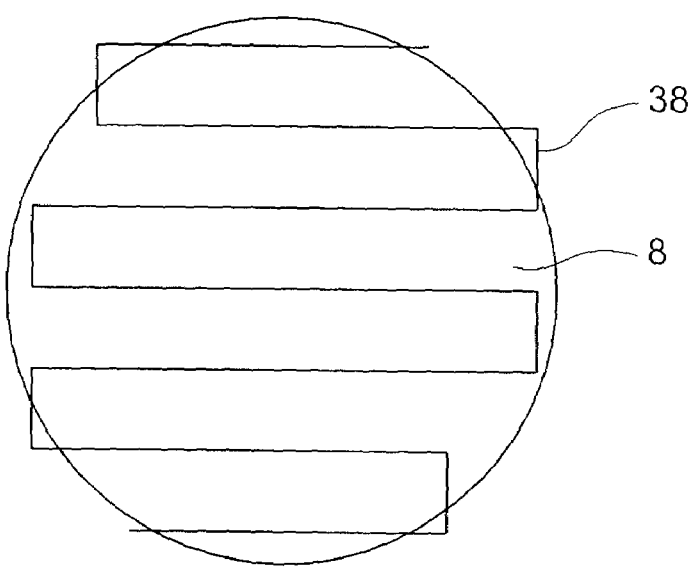
FIG. 5 is a schematic diagram in which another example of a path of a nozzle relative to a semiconductor wafer is shown.

Moreover, the example shown in FIG. 5 may also be used for the path 38 of the nozzle 20.

In this example, the nozzle 20 is moved widely in a transverse direction of the semiconductor wafer 8 and a little at a time in a vertical direction. Wasteful movement is suppressed by moving along the sensor chips 29, since gas is not emitted in places where there are no sensor chips 29, enabling breaking strength inspection of all of the sensor chips 29 to be made in a shorter time.

Figure 6:
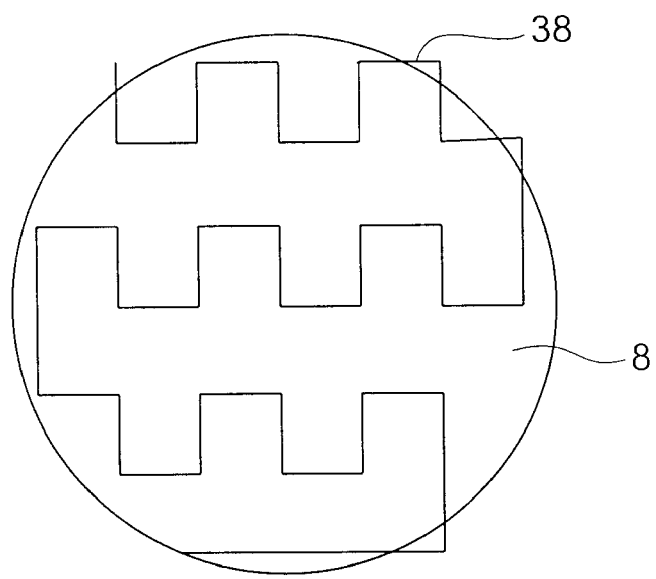
FIG. 6 is a schematic diagram in which another example of a path of a nozzle relative to a semiconductor wafer is shown.

The example shown in FIG. 6 may also be used. In this example, the nozzle 20 is moved little by little both vertically and horizontally. In this example, wasteful movement is also suppressed in a similar manner to that of FIG. 5, enabling breaking strength inspection of all of the sensor chips 29 to be made in a shorter time.

Now, the nozzle 20 shown in FIG. 1 is a single nozzle 20, and is an example in which a single nozzle 20 is used to perform a breaking strength inspection on all of the sensor chips 29, but when only one nozzle 20 is used, the area over which a medium such as gas, water, etc., can be applied at a uniform pressure is limited. As a result, it takes a long time to inspect the sensor chips 29 over the entire surface of the semiconductor wafer 8.

Figure 7:
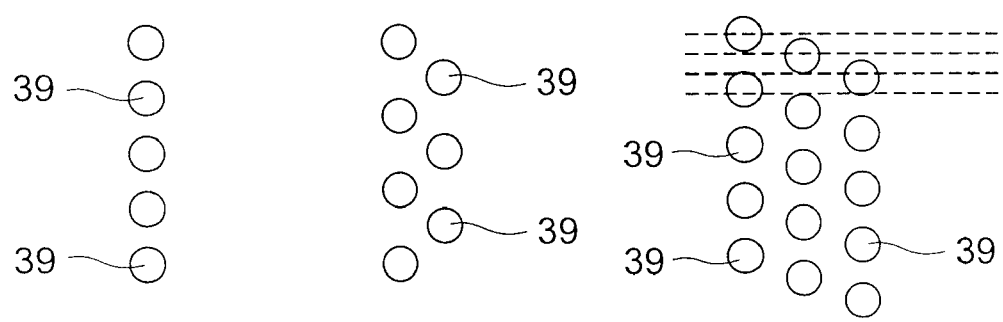
FIG. 7 is a schematic diagram in which an arrangement of a plurality of nozzles is shown.

As shown in FIG. 7, by gathering together a plurality of nozzles 20, and disposing the nozzles 20 such that their respective emitting apertures 39 form a single straight row, or disposing the nozzles 20 alternately in two rows such that the emitting apertures 39 do not overlap each other, or disposing them in three rows, etc., it becomes possible to shorten the time required for inspection of the breaking strength of all of the sensor chips 29.

Figure 8:
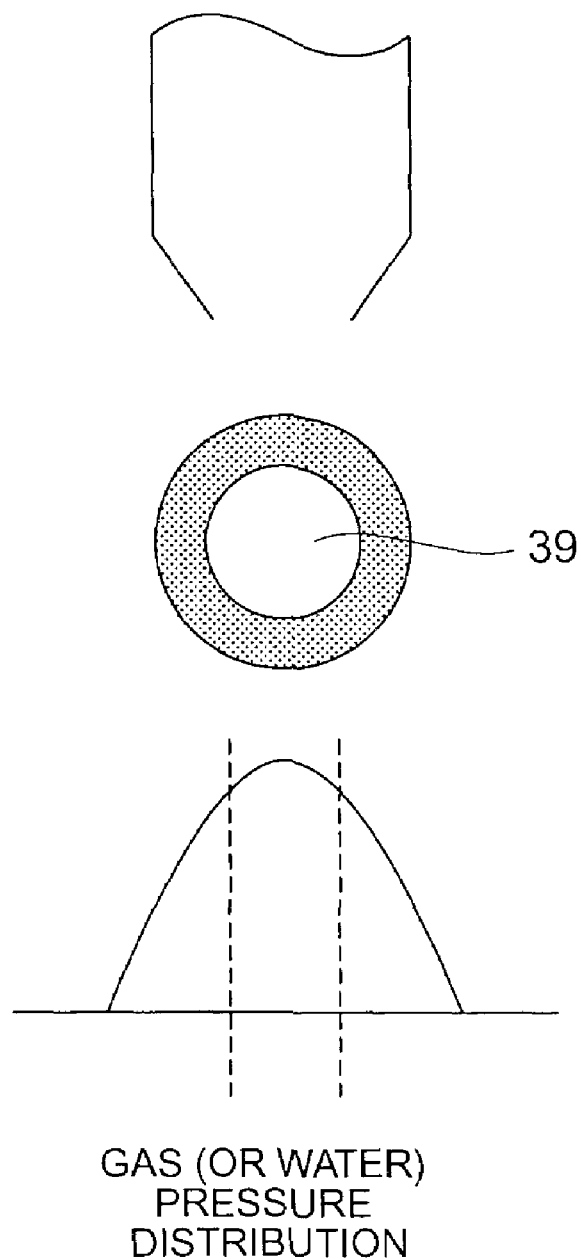
FIG. 8 is a schematic diagram in which an example of a nozzle shape is shown.
Figure 9:
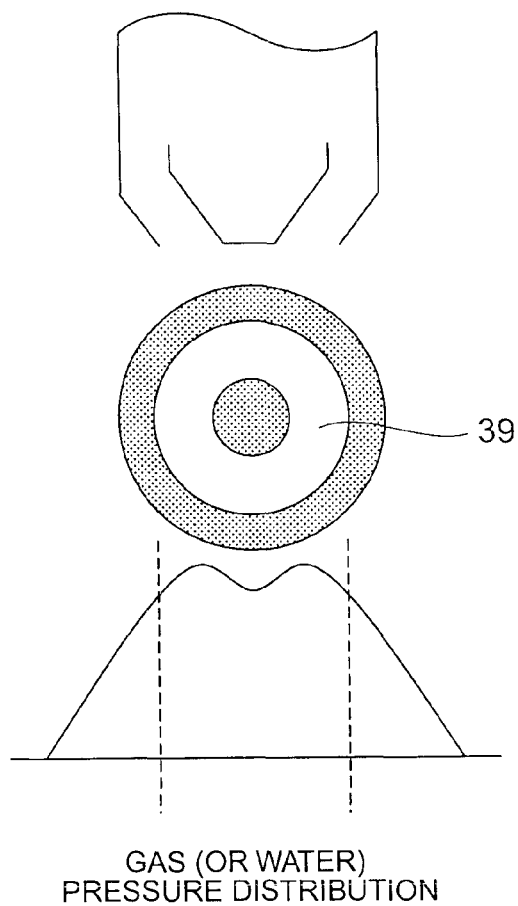
FIG. 9 is a schematic diagram in which another example of a nozzle shape is shown.

Moreover, the emitting aperture 39 of the nozzle 20 shown in FIG. 1 is a circular emitting aperture 39 as shown in FIG. 8, making a uniform pressure region narrow, but the uniform pressure region can be widened by forming the emitting aperture 39 so as to have a doughnut shape as shown in FIG. 9, improving inspection efficiency of the breaking strength of the sensor chips 29 proportionately.

Figure 10:
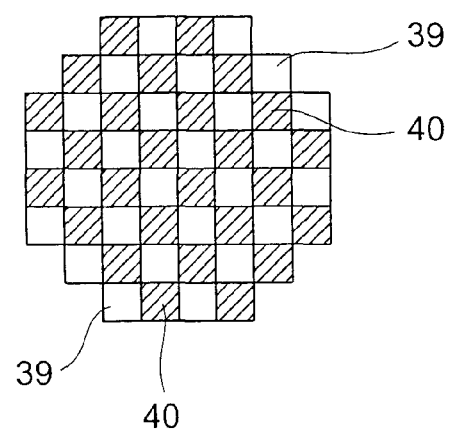
FIG. 10 is a schematic diagram in which an example of a nozzle emitting aperture is shown.
Figure 11:
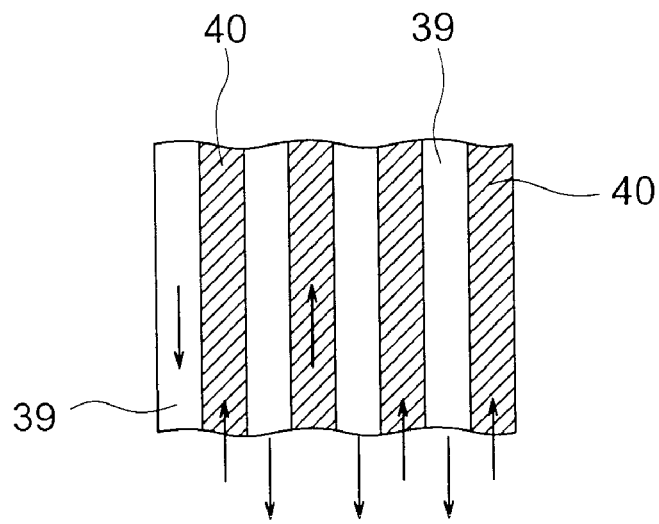
FIG. 11 is a schematic diagram in which a cross section of nozzle from FIG. 10 is shown.

FIGS. 10 and 11 show an example in which the area of the semiconductor wafer 8 is large, and a plurality of nozzles 20 used therein are bundled together. If the nozzles 20 are bundled together without modification, medium that is emitted from nozzles 20 that are positioned centrally has nowhere to run off, and as a result the uniform pressure region decreases.

In this example, nozzles 20 that have suction apertures 40 surround the nozzles 20 from which the medium is emitted. As a result, medium that has been emitted from the emitting apertures 39 is sucked in through the suction apertures 40 of the adjacent nozzles 20, enabling the medium to flow smoothly and pressure to be applied to the entire surface of the large-area semiconductor wafer 8 uniformly.

Figure 12:
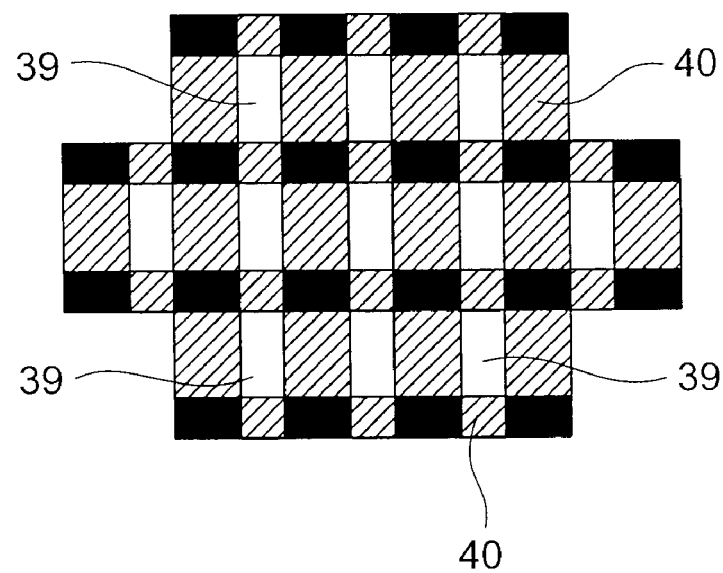
FIG. 12 is a schematic diagram in which another example of a nozzle emitting aperture is shown.

FIG. 12, in particular, shows an example in which the emitting apertures 39 of each of the nozzles 20 are disposed so as to be aligned with the arrangement of the sensor chips 29. In this example, nozzles 20 that have suction apertures 40 also surround the nozzles 20 from which the medium is emitted.

In this configuration, breaking strength inspection of all of the sensor chips 29 can be performed simultaneously, significantly improving inspection efficiency, and making cost reducing effects large.

Embodiment 2

Figure 13:
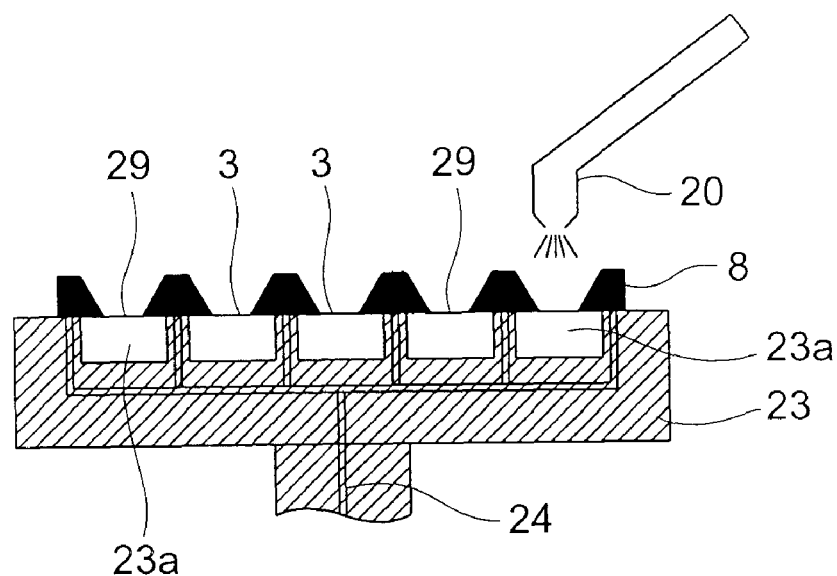
FIG. 13 is a schematic diagram in which a cross section of a sensor chip breaking strength inspection apparatus according to Embodiment 2 of the present invention is shown.

FIG. 13 is a schematic diagram showing a cross section of a sensor chip breaking strength inspection apparatus according to the present invention.

In this embodiment, a semiconductor wafer 8 is mounted onto a stage 23 with the semiconductor wafer 8 turned upside down. Grooves 23a are formed on the stage 23 so as to correspond to sensor chips 29 in order to prevent patterned circuits formed on a front surface of the semiconductor wafer 8 from being placed in contact with the stage 23.

The rest of the configuration is similar to that of Embodiment 1, and this embodiment can also achieve effects similar to those of Embodiment 1.

Embodiment 3

Figure 14:
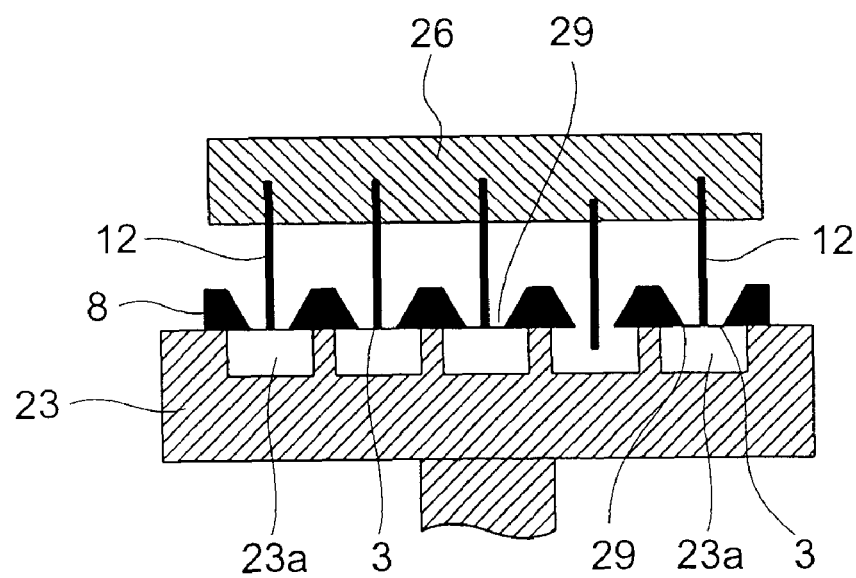
FIG. 14 is a schematic diagram in which a cross section of a sensor chip breaking strength inspection apparatus according to Embodiment 3 of the present invention is shown.

FIG. 14 is a schematic diagram showing a cross section of a sensor chip breaking strength inspection apparatus according to the present invention.

A sensor chip breaking strength inspection apparatus according to this embodiment includes: a stage 23 for mounting a semiconductor wafer; probes 12 that apply to a sensor chip 29 a pressing force equivalent to the standard breaking strength of the sensor chip 29; and a pressurization and displacement measuring apparatus 26 that applies pressure to the probes 12 and measures displacement of the probes 12. Grooves 23a are formed on the stage 23 so as to correspond to each of the sensor chips 29.

In this sensor chip breaking strength inspection apparatus, the probes 12 are pushed onto the rear surface of the semiconductor wafer at the standard breaking strength value of the sensor chips 29, and because sensor chips 29 that are at less than or equal to the standard breaking strength will break, properties of the sensor chips 29 can be inspected using the probes 12, and breaking strength inspection also becomes possible. Because the probes 12 are disposed so as to be equal in number to the sensor chips 29, breaking strength inspection of all of the sensor chips 29 on the semiconductor wafer 8 can be performed simultaneously, improving inspecting efficiency and making cost reducing effects large.

Embodiment 4

Figure 15:
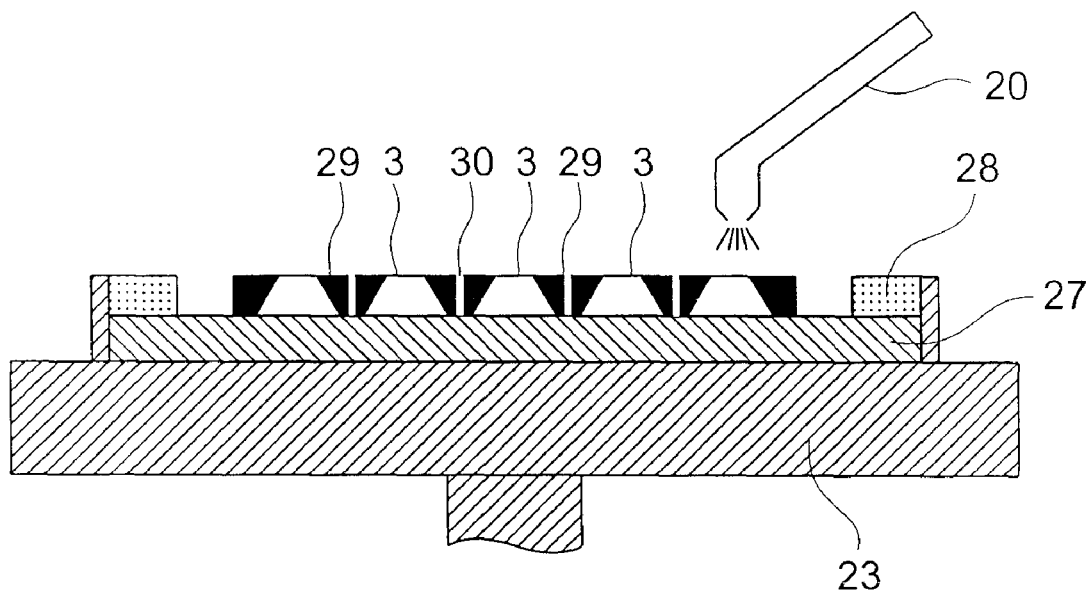
FIG. 15 is a schematic diagram in which a cross section of a sensor chip breaking strength inspection apparatus according to Embodiment 4 of the present invention is shown.

FIG. 15 is a schematic diagram showing a cross section of a sensor chip breaking strength inspection apparatus according to the present invention.

An inspection apparatus according to this embodiment is used in a cleaning process after a semiconductor wafer 8 is affixed to dicing tape 27 of a dicing tape ring 28 and diced.

In this embodiment, sensor chips 29 that are separated by grooves 30 that are formed by dicing of the semiconductor wafer 8 are affixed to the dicing tape 27, and breaking strength inspection of the sensor chips 29 can also be performed at the same time as a cleaning process for dicing residue by emitting water or cleaning liquid having a pressure equivalent to the standard breaking strength of the sensor chips 29 from a nozzle 20 toward the sensor chips 29, making it unnecessary to set up a breaking strength inspecting process separately for the sensor chips 29.

Embodiment 5

In inspection apparatuses according to Embodiments 1 through 4, presence or absence of breakage of the sensor chips 29 was performed by naked eye, but in this embodiment, a breakage presence or absence detecting means for detecting the presence or absence of breakage of the sensor chips 29 is further included.

Figure 16:
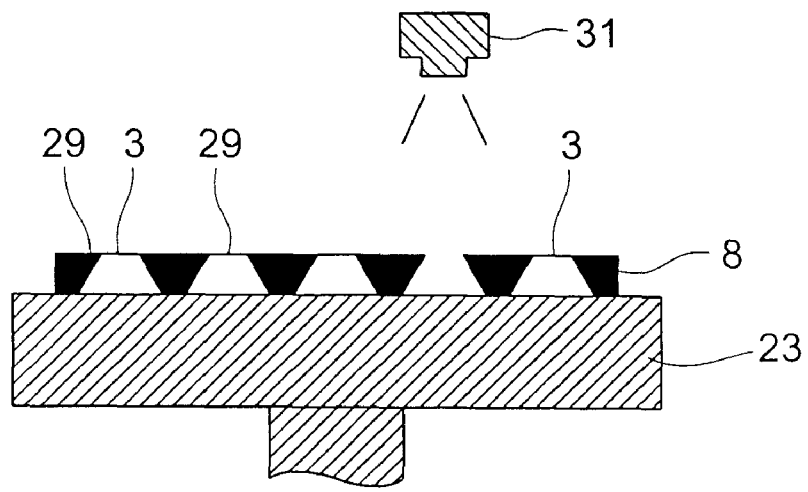
FIG. 16 is a schematic diagram in which a cross section of a breakage presence or absence detecting means of a sensor chip breaking strength inspection apparatus according to Embodiment 5 of the present invention is shown.

FIG. 16 is a schematic diagram showing a breakage presence or absence detecting means in a sensor chip breaking strength inspection apparatus according to the present invention.

In this breakage presence or absence detecting means, an image recognizing apparatus 31 that optically recognizes breakage of the sensor chips 29 is disposed above the semiconductor wafer 8.

Moreover, additional examples of breakage presence or absence detecting means include those shown in FIGS. 17 through 21.

Figure 17:
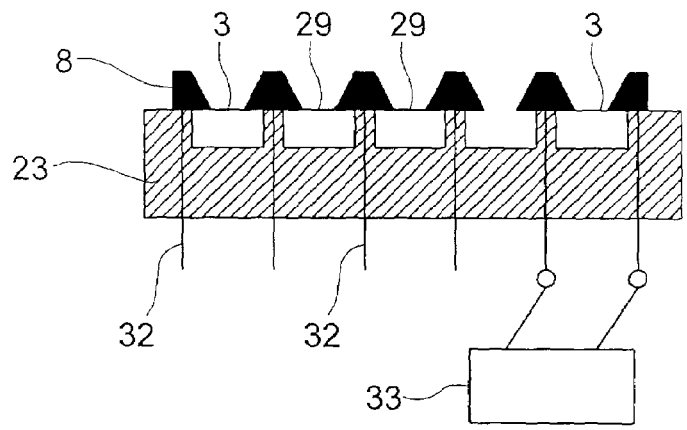
FIG. 17 is a schematic diagram in which a cross section of an example differing from the breakage presence or absence detecting means from FIG. 16 is shown.

The breakage presence or absence detecting means shown in FIG. 17 includes: electrodes 32 that are disposed on a stage 23 and that come into contact with pad portions of a patterned circuit formed on a front surface of each of the sensor chips 29; and a resistance measuring device 33 that is electrically connected between these electrodes 32 so as to measure resistance between the pad portions.

Figure 18:
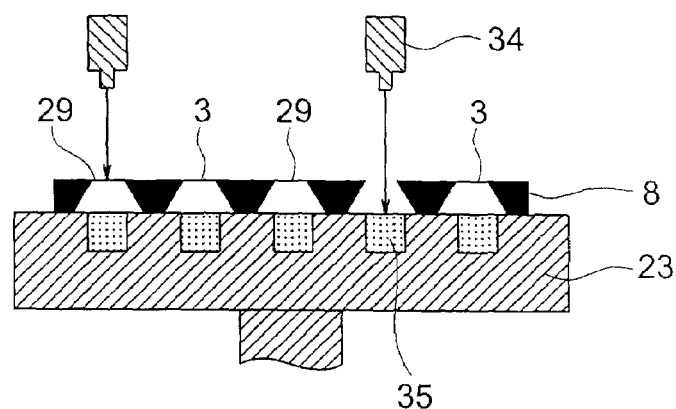
FIG. 18 is a schematic diagram in which a cross section of an example differing from the breakage presence or absence detecting means from FIG. 16 is shown.

The breakage presence or absence detecting means shown in FIG. 18 includes: a photoemitter 34 that directs light at a sensor chip 29 that has an opaque pattern formed on a front surface; and a photodetector 35 that is disposed on an opposite side of the sensor chip 29 from the photoemitter 34 and detects light from the photoemitter 34 that has passed through the sensor chip 29.

Figure 19:
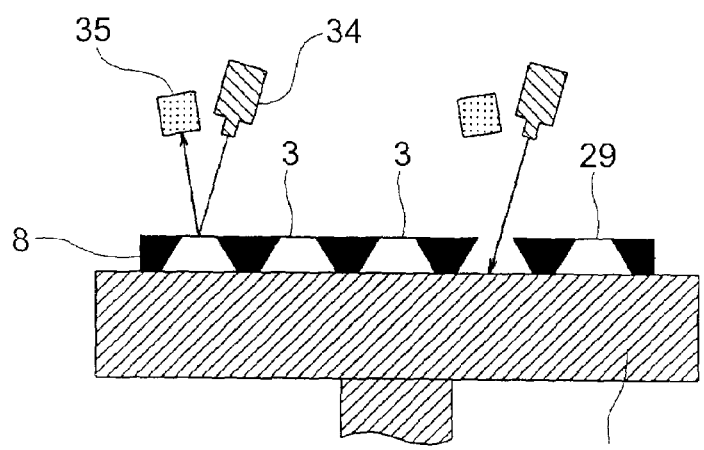
FIG. 19 is a schematic diagram in which a cross section of an example differing from the breakage presence or absence detecting means from FIG. 16 is shown.

The breakage presence or absence detecting means shown in FIG. 19 includes: a photoemitter 34 that directs light at a sensor chip 29; and a photodetector 35 that detects light from the photoemitter 34 that has been reflected by a light-reflecting pattern that is formed on a front surface of the sensor chip 29.

Figure 20:
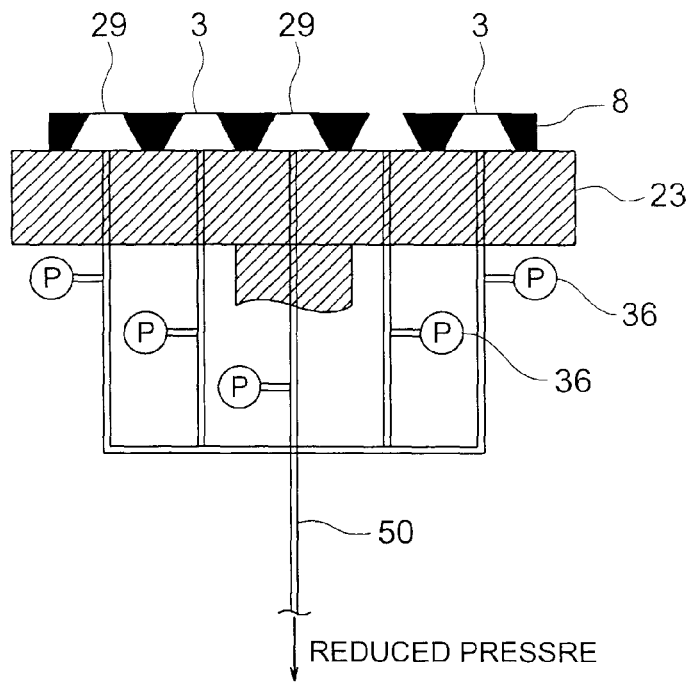
FIG. 20 is a schematic diagram in which a cross section of an example differing from the breakage presence or absence detecting means from FIG. 16 is shown.

The breakage presence or absence detecting means shown in FIG. 20 includes: a suction pipe 50 that passes through a stage 23 and has tip portions that are directed at the sensor chips 29; and pressure gauges 36 that are connected to the suction pipe 50 and constitute a medium detector that detects a medium.

Figure 21:
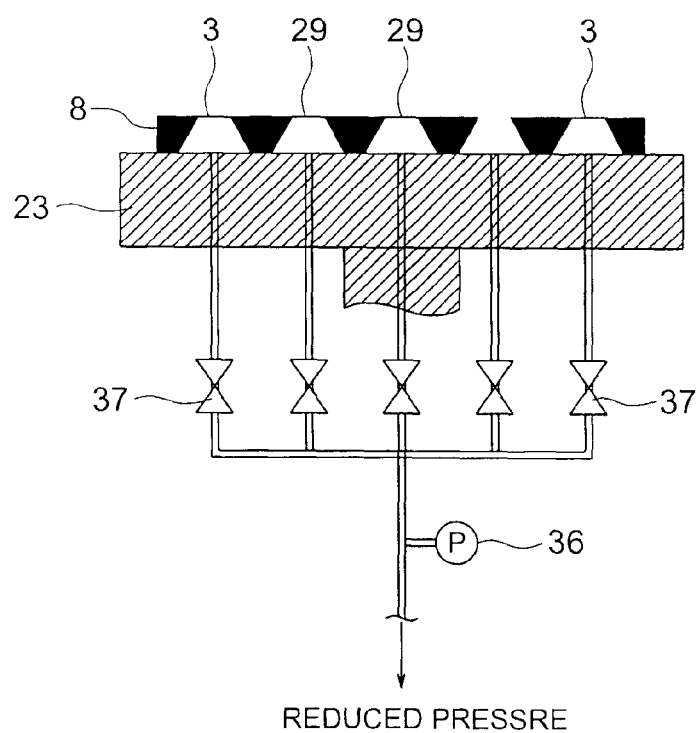
FIG. 21 is a schematic diagram in which a cross section of an example differing from the breakage presence or absence detecting means from FIG. 16 is shown.

The breakage presence or absence detecting means shown in FIG. 21 includes: a suction pipe 50 that passes through a stage 23 and has tip portions that are directed at the sensor chips 29; valves 37 that are connected to the suction pipe 50; and a medium detector 36 that detects a medium.

In the configurations in FIGS. 20 and 21, a rear side of the diaphragm portions 3 and 25 is kept at slightly reduced pressure in both cases.

In the case of the configuration in FIG. 20, simultaneous inspection is possible, but a pressure gauge 36 is required for each of the sensor chips 29.

In this example, if a sensor chip 29 breaks, the broken sensor chip 29 can be detected easily since the value at the pressure gauge 36 corresponding to that sensor chip 29 will differ from those of the other pressure gauges 36.

In the case of the configuration in FIG. 21, broken sensor chips 29 can be detected easily by switching among each of the valves 37 and monitoring the condition of each of the sensor chips 29 sequentially.

If a gas such as Ar, He, etc., for example, is mixed into the emitted gas in advance, and a mass spectrometer is used for the medium detector instead of the pressure gauge 36, broken sensor chips 29 can be detected easily since the gas such as Ar, He, etc., can be detected from the broken sensor chips 29 in addition to the usual nitrogen and oxygen.

If pure water is used for the medium, and constituents that conduct electricity (such as ammonia, hydrogen peroxide, carbon dioxide, etc.) are mixed into the pure water, and a resistance measuring device is used for the medium detector, then broken sensor chips 29 can be detected easily since the liquid that conducts electricity can be detected from the broken sensor chips 29.

Thus, a determination of suitability of each of the sensor chips 29 can be performed accurately by adding any of the breakage presence or absence detecting means to the sensor chip breaking strength inspection apparatuses according to Embodiments 1 through 4 above.

What is claimed is:

1. A sensor chip breaking strength inspection apparatus that performs sensor chip breaking strength inspection on a semiconductor wafer on which a plurality of sensor chips having a diaphragm portion are disposed, characterized in that said sensor chip breaking strength inspection apparatus comprises:
a stage on which said semiconductor wafer is mounted; and
a nozzle that emits a medium onto said sensor chips at a pressure equivalent to a standard breaking strength of said sensor chips.

2. A sensor chip breaking strength inspection apparatus according to claim 1, wherein said pressure of said medium that is emitted from said nozzle is greater than or equal to atmospheric pressure.

3. A sensor chip breaking strength inspection apparatus according to claim 1, wherein said nozzle and said semiconductor wafer are moved relative to each other such that said medium is emitted over an entire surface of said semiconductor wafer.

4. A sensor chip breaking strength inspection apparatus according to claim 1, wherein a plurality of said nozzles are disposed, and emitting apertures of said nozzles are disposed in a straight line and directed at a surface of said semiconductor wafer.

5. A sensor chip breaking strength inspection apparatus according to claim 1, wherein an emitting aperture of said nozzle has a doughnut shape.

6. A sensor chip breaking strength inspection apparatus according to claim 1, wherein a plurality of said nozzles are disposed, and nozzles having a suction aperture surround a nozzle having an emitting aperture.

7. A sensor chip breaking strength inspection apparatus according to claim 6, wherein said emitting aperture faces said sensor chips.

8. A sensor chip breaking strength inspection apparatus according to claim 1, further comprising a breakage presence or absence detecting means that detects presence or absence of breakage in said sensor chips after said pressure has been applied to said sensor chips.

9. A sensor chip breaking strength inspection apparatus according to claim 8, wherein said breakage presence or absence detecting means is an image recognizing apparatus that optically recognizes breakage in said sensor chips.

10. A sensor chip breaking strength inspection apparatus according to claim 8, wherein said breakage presence or absence detecting means comprises:
   electrodes that are disposed on said stage and come into contact with pad portions of a patterned circuit that is formed on a front surface of each of said sensor chips; and
   a resistance measuring device that is electrically connected between said electrodes and measures resistance between said pad portions.

11. A sensor chip breaking strength inspection apparatus according to claim 8, wherein:
   said sensor chips have an opaque pattern formed on a front surface; and
   said breakage presence or absence detecting means comprises:
      a photoemitter that directs light at said sensor chips; and
      a photodetector that is disposed on an opposite side of said sensor chips from said photoemitter and detects light from said photoemitter that has passed through said sensor chips.

12. A sensor chip breaking strength inspection apparatus according to claim 8, wherein said breakage presence or absence detecting means comprises:
   a photoemitter that directs light at said sensor chips; and
   a photodetector that detects light from said photoemitter that has been reflected by a light-reflecting pattern that is formed on a front surface of said sensor chips.

13. A sensor chip breaking strength inspection apparatus according to claim 8, wherein said breakage presence or absence detecting means comprises:
   a suction pipe that passes through said stage and has a tip portion that is directed at said diaphragm portion; and
   a medium detector that is connected to said suction pipe and detects said medium.

14. A sensor chip breaking strength inspection method characterized in that a sensor chip breaking strength inspection is performed while cleaning during or after dicing of a semiconductor wafer on which a plurality of sensor chips having a diaphragm portion are disposed, said sensor chip breaking strength inspection being performed by emitting a medium at said sensor chips at a pressure equivalent to a standard breaking strength of said sensor chips.

* * * * *